United States Patent
Patel et al.

(10) Patent No.: US 9,452,035 B2
(45) Date of Patent: Sep. 27, 2016

(54) DEVICE TO PROVIDE ENHANCED FLOSSING BENEFITS

(75) Inventors: Madhusudan Patel, Somerset, NJ (US); John J. Gatzemeyer, Hillsborough, NJ (US); Eduardo J. Jimenez, Manalapan, NJ (US); Sharon Kennedy, Randallstown, MD (US)

(73) Assignee: COLGATE-PALMOLIVE COMPANY, New York, NY (US)

( * ) Notice: Subject to any disclaimer, the term of this patent is extended or adjusted under 35 U.S.C. 154(b) by 238 days.

(21) Appl. No.: 13/983,236

(22) PCT Filed: Feb. 1, 2011

(86) PCT No.: PCT/US2011/023371
§ 371 (c)(1),
(2), (4) Date: Aug. 1, 2013

(87) PCT Pub. No.: WO2012/105965
PCT Pub. Date: Aug. 9, 2012

(65) Prior Publication Data
US 2013/0316070 A1 Nov. 28, 2013

(51) Int. Cl.
*A61C 15/04* (2006.01)

(52) U.S. Cl.
CPC .......... *A61C 15/043* (2013.01); *A61C 15/046* (2013.01); *A61C 15/041* (2013.01)

(58) Field of Classification Search
CPC .. A61C 15/04; A61C 15/043; A61C 15/046; A61C 15/041
USPC ....... 132/324, 325, 322; 206/63.5, 225, 226; 427/2.29
See application file for complete search history.

(56) References Cited

U.S. PATENT DOCUMENTS

| | | | | |
|---|---|---|---|---|
| 1,953,863 A | * | 4/1934 | Morrell | B65H 71/007 118/220 |
| 2,128,701 A | | 8/1938 | Ernst | |
| 2,800,779 A | * | 7/1957 | Karl | D04B 5/22 242/154 |
| 3,830,247 A | * | 8/1974 | Kaphalakos | A61C 15/043 132/322 |
| 3,902,510 A | * | 9/1975 | Roth | 132/322 |
| 3,942,539 A | | 3/1976 | Corliss et al. | |
| 4,019,522 A | | 4/1977 | Elbreder | |
| 4,162,688 A | * | 7/1979 | Tarrson | A61C 15/043 132/322 |
| 4,254,645 A | * | 3/1981 | Kouris | D05B 91/00 112/270 |

(Continued)

FOREIGN PATENT DOCUMENTS

EP 0080440 6/1983

OTHER PUBLICATIONS

International Search Report and Written Opinion of the International Searching Authority issued in International Application No. PCT/US2011/023371 mailed Nov. 8, 2011.

*Primary Examiner* — Tatiana Nobrega

(57) ABSTRACT

A dental floss dispenser having a wicking delivery system with a reservoir for storing a solution of oral care ingredients generally in fluid form. The reservoir includes an absorbent wicking porous pad that extends through at least a portion of the floss dispensing device to deliver the solution to the dental floss. When the floss is pulled through the porous pad holding the oral care ingredient(s), the porous pad activates (e.g., coats, impregnates, saturates) the floss, providing the consumer with new benefits such as enhanced deep cleaning, new flavors, better plaque dissolving capabilities, ease of floss use and maneuverability, whitening, and deposition of therapeutic actives into the gum pockets.

4 Claims, 3 Drawing Sheets

(56) References Cited

U.S. PATENT DOCUMENTS

| | | | |
|---|---|---|---|
| 4,673,106 A | 6/1987 | Fishman | |
| 4,875,348 A * | 10/1989 | Kinnebrew, II | D05B 67/00 112/270 |
| 5,065,861 A | 11/1991 | Greene et al. | |
| 5,076,302 A | 12/1991 | Chari | |
| 5,582,195 A | 12/1996 | Nagel | |
| 5,680,876 A | 10/1997 | Hasham et al. | |
| 5,755,243 A | 5/1998 | Roberts et al. | |
| 5,896,868 A * | 4/1999 | Kyte | A61C 15/043 118/420 |
| 5,904,152 A | 5/1999 | Tseng et al. | |
| 5,911,829 A * | 6/1999 | Maksudian | A61B 17/06123 118/123 |
| 6,536,448 B2 | 3/2003 | McDevitt et al. | |
| 6,705,328 B1 * | 3/2004 | Ramirez | A61C 15/043 132/322 |
| 6,926,010 B1 | 8/2005 | Sofie | |
| 6,971,879 B2 | 12/2005 | Discko, Jr. | |
| 7,168,707 B2 | 1/2007 | Casey et al. | |
| 8,256,439 B1 * | 9/2012 | Stinson | A61C 15/043 132/324 |
| 2008/0190787 A1 | 8/2008 | Grosse | |
| 2008/0257377 A1 * | 10/2008 | Burrows | A61C 15/043 132/322 |

* cited by examiner

DEVICE TO PROVIDE ENHANCED FLOSSING BENEFITS

CROSS-REFERENCE TO RELATED PATENT APPLICATIONS

The present application is a U.S. national stage application under 35 U.S.C. §371 of PCT Application No. PCT/US2011/023371, filed Feb. 1, 2011, the entirety of which is incorporated herein by reference.

FIELD OF THE INVENTION

The present invention relates generally to dispensers for dental floss, and more specifically, to dental floss string containers having wicking members to coat the floss prior to dispensing.

BACKGROUND OF THE INVENTION

Current dental floss string containers serve simply to house the floss string, its spool and in some cases, help facilitate the cutting of the floss string to a desired length via a sharpened bevel on one side of the floss container.

Despite daily brushing and rinsing with anti-bacterial mouthwashes, the surfaces between teeth are still prone to cavities. As a result, interproximal cleaning devices such as dental floss and interdental brushes have been highly touted and recommended by the dental profession for effective oral hygiene. The devices are however insufficient, particularly with regards to stubborn plaque removal, ease of use, and overall consumer experience.

Moreover, despite the plethora of beneficial oral care ingredients and actives that could be incorporated into floss string, there is still not yet a universal, rapid method to effectively impregnate a variety of different actives into the floss string. Moreover, methods that assert to do so are hampered by high cost, issues with manufacture and processability of the fibre, and its long-term stability.

While these teachings may overcome some of these issues and hurdles, without major upheaval in the daily oral care habits and practices of the consumer, they still leave much to be desired. For example, the current attempts are insufficient due to costs, fluid leakage or high effort requirements to pull floss through overly restrictive passages in an attempt to keep the passages fluid tight, even causing breakage of the floss inside the dispenser. Thus it would be beneficial to provide a dispenser that rapidly coats or activates the floss with oral care ingredients as the floss is unwound from its spool and easily pulled through the floss dispenser while preventing fluid leakage within the dispenser.

BRIEF SUMMARY OF THE INVENTION

The present invention pertains to an oral care dispenser having a capillary delivery system with a reservoir for storing a solution of oral care ingredients generally in fluid form. The reservoir includes an absorbent wicking porous pad constructed from a fibrous material, ceramic, porous plastic, or combination thereof that extends through at least a portion of the floss dispensing device to deliver the solution to the dental floss.

In accordance with an example of the preferred embodiments, the invention includes A dental floss device comprising a housing having a floss access port; a dental floss positioned within the housing and extending through the floss access port; and a wicking member containing an oral care fluid, wherein a portion of the dental floss is in contact with the wicking member.

In accordance with another example of the preferred embodiments, the invention includes a dental floss device, comprising a housing having a floss access port through which dental floss can be dispensed; a spool of the dental floss positioned within the housing; and a first wicking member containing a first oral care fluid, the dental floss extending from the spool and adjacent the first wicking member toward the floss access port, the first wicking member providing delivery of the first oral care fluid to the dental floss adjacent the first wicking member as the dental floss is pulled through the access port.

In accordance with another example of the preferred embodiments, the invention includes a method of coating floss in situ comprising the steps of a) providing a dental floss device comprising a housing having a floss access port; a dental floss positioned within the housing and extending through the floss access port; and a wicking member containing an oral care fluid, wherein a portion of the dental floss is in contact with the wicking member; and b) pulling the dental floss through the floss access port, wherein the oral care fluid has been applied to the dental floss.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein.

DETAILED DESCRIPTION OF THE INVENTION

Figure 1:
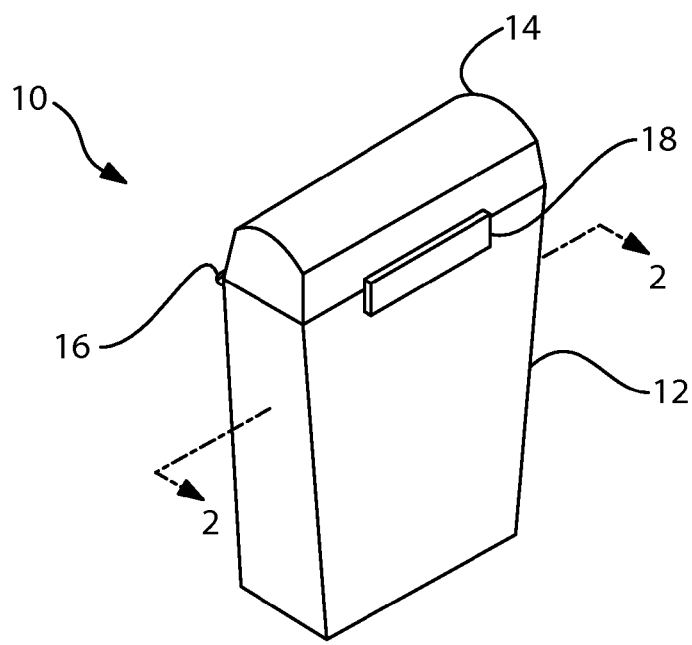
FIG. 1 is a perspective view of an exemplary dental floss dispenser constructed in accordance with the invention.

The following description of the preferred embodiment(s) is merely exemplary in nature and is in no way intended to limit the invention, its application, or uses.

As used throughout, ranges are used as a shorthand for describing each and every value that is within the range. Any value within the range can be selected as the terminus of the range. In addition, all references cited herein are hereby incorporated by reference in their entireties. In the event of a conflict in a definition in the present disclosure and that of a cited reference, the present disclosure controls.

Unless otherwise specified, all amounts, quantities, and geometric features expressed herein and elsewhere in the specification should be understood to include substantial approximations of the express term. For example, the term "cylindrical" should be understood as including generally or approximately cylindrical configurations.

The exemplary floss dispensers include a dental floss activating chamber or container that can carry different oral care ingredients in fluid form (e.g., liquid, gel, solid particle solution) immersed in a porous pad in contact with the floss string. When the floss is pulled through the porous pad impregnated with or holding the oral care ingredient(s), the porous pad activates (e.g., coats, impregnates, saturates) the floss, providing the consumer with new benefits such as enhanced deep cleaning, new flavors, better plaque dissolving capabilities, ease of floss use and maneuverability, whitening, and deposition of therapeutic actives into the gum pockets. The absorbent wicking action of the porous pad keeps the oral care ingredient(s) carrying fluid (also referred to as oral care fluid) in the chamber even when floss access ports of the chamber are not restrictively leak-proof.

Oral care ingredients within the scope of the invention can include, but are not limited to flavors, sensates (e.g., warming, cooling, tingling, popping) or actives that are hard to formulate into a mouthrinse or toothpaste, but are stable and robust enough in a concentrated liquid, gel, solid particle solution contained in the porous pad within the floss dispenser. The oral care ingredient(s) could also be activated on a second floss string that is then spirally wound around the first floss string in ropelike fashion to bring together the benefits of two or more dental floss strings into one. As an example one floss string may offer increased abrasiveness for enhanced cleaning and a second string could release actives between teeth.

In greater particularity, non-limiting examples of fluids or oral care agents which can be used as the oral care fluid include antibacterial agents, whitening agents, anti-sensitivity agents, anti-inflammatory agents, anti-attachment agents, plaque indicator agents, flavorants, sensates, and colorants. Examples of these agents are within the knowledge of those skilled in the art.

The oral care agent or ingredient(s) can be provided in any suitable vehicle, such as in aqueous solution or in the form of gel or paste. Non-limiting examples of vehicles include water, monohydric alcohols such as ethanol, poly(ethylene oxides) such as polyethylene glycols such as PEG 2M, 5M, 7M, 14M, 23M, 45M, and 90M available from Union Carbide, carboxymethylene polymers such as Carbopol® 934 and 974 available from B.F. Goodrich, and combinations thereof. The selection of a suitable vehicle will be apparent to persons skilled in the art depending on such factors as the properties of the oral care agent and the desired properties of the medium, such as viscosity.

Porous wicking materials, like sponges and wicks, absorb and hold fluid, and upon sufficient contact or pressure release the fluid. The preferred embodiments capitalize on this property and incorporate it into the floss dispenser. Upon contact with the floss string, the porous pad releases liquid that coats or impregnates the floss string before it exits the floss housing.

The wicking material will be constructed from polymers such as polyethylene, polypropylene, celluloses, wools, polyesters, collagens, nylons and blends thereof. The dental floss activating chamber or container includes a porous pad as a wicking member (e.g., wick, sponge, absorbent fibre or other absorbent materials) impregnated with or holding oral care ingredients as discussed above. While not being limited to a particular theory, the floss, which is preferably not pre-waxed for greater absorption potential, is continuously thread through the porous pad, as can be seen in the figures. In particular, the floss is drawn through the wicking member or porous pad holding the oral care fluid. The fluid in the porous pad activates (e.g., coats, impregnates, saturates) the floss as it is drawn through the pad. The system can be designed such that the liquid is drawn into the floss through favorable ionic interactions, capillary action, porosities in the floss string, or as the floss travels through the porous pad there is a slight pressure on the pad causing fluid to be released onto the floss. The porous pad could also be made from hydrogels that release actives as the floss is drawn through the hydrogel pad or strip.

Figure 6:
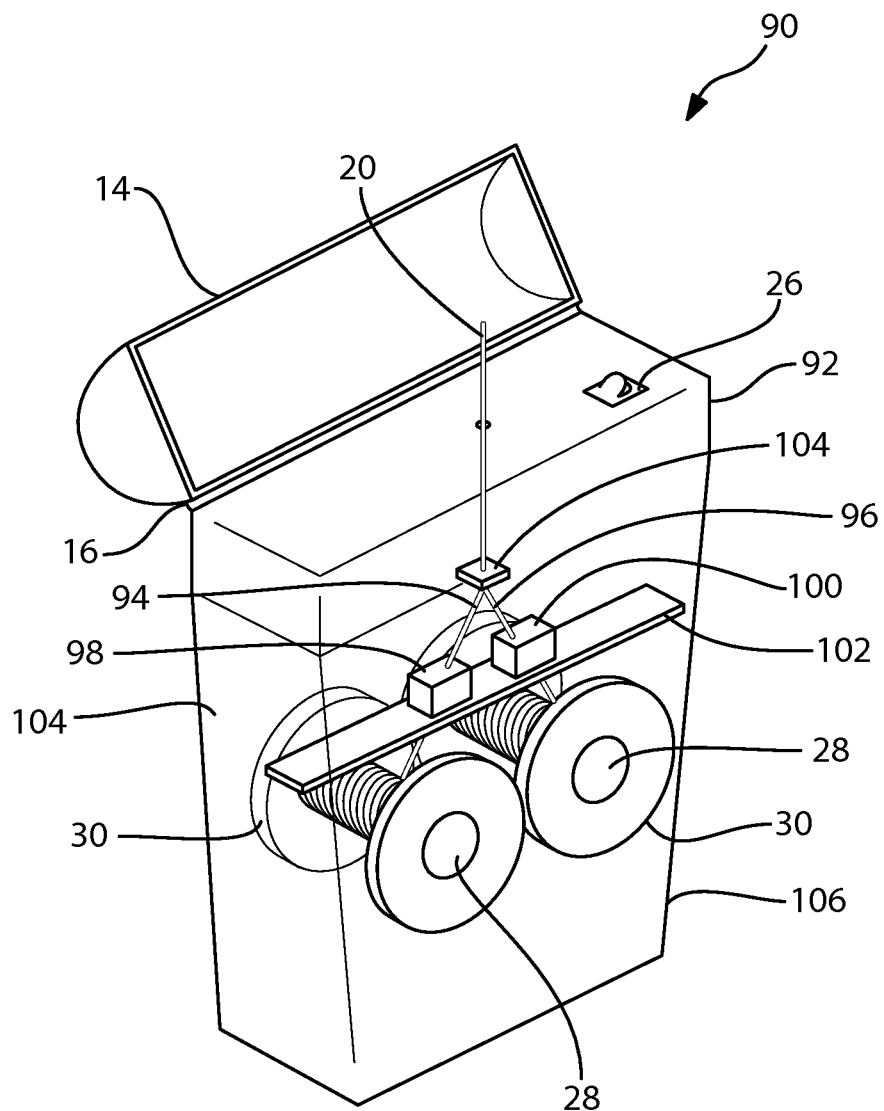
FIG. 6 is a perspective view of a fourth exemplary dental floss dispenser constructed in accordance with the invention.

The porous pad is preferably separated from the floss spool in another separate chamber. The porous pad could also be wrapped with a clear sheath to help hold the fluid within the wicking member. If desired, the amount of fluid remaining in the porous pad can be revealed through a clear window designed into the side of the container (FIG. 6). The floss container can be used replenished with oral care ingredients or until the floss spool is emptied.

The exemplary embodiments also contemplate more than one porous pad (FIGS. 2 and 6); each generally saturated with different oral care ingredients. As noted above, replacement oral care fluid porous pads could also be used within the floss dispenser. Different porous pads would provide different benefits such as flavors, strength of plaque dissolving abilities, for example by use of different oral care fluids.

As another example, there may be more than one dental floss activating chamber or container within the floss dispenser (FIG. 2), with at lease one of the activating chambers including a porous pad at least partially saturated with an oral care ingredient, such as a liquid, gel, or solid particle solution, allowing multiple actives or reactions to occur as the floss string is drawn through the respective porous pad. Different chambers may offer different properties to the floss. Any of the chambers could also serve as mixing or reaction chambers.

While not being limited to a particular theory, the dental floss activating chamber or porous pad therein may be disposable, refillable, and/or interchangeable with other like members containing different fluids, for example. The chamber/porous pad could also serve as a depository for mouthrinses through which the floss could be pulled through, priming the floss string before use.

The exemplary porous pad(s) may be formed from any suitable material and may include reticulated foam, which may range from hydrophilic to hydrophobic. Hydrophobic foams may be used with non-water based liquids. An example of a reticulated foam is Bulpren S90, manufactured by Recticel (Wetteren, Belgium). Bulpren S90 is an open cell polyurethane foam based on polyester which averages 90 pores per inch. Hydrophilic foams may be used with water based liquids. Other examples of materials that can be used for the porous pad include ceramics, porous plastics, natural sponge and even wood or resin fiber. In a preferred embodiment, the reservoir may be a commercially available bonded fiber component from Filtrona or Porex, such as without limitation polypropylene, polyethylene, or copolymers of such polymers in varying ranges of hydrophobicity depending on the composition selected.

The exemplary floss string can be made of materials that will ease its coating of actives, or ease the penetration of the floss string as it is gently pulled through the active reservoir. Preferably the floss is unwaxed before activation by the oral care fluid.

The rate and amount of fluid released from the porous pad to the dental floss will be governed by the chemical and physical properties of the porous pad and floss, including volume holding capacity of the pad and floss material as well as pressure applied on the pad during use. The porous materials can be treated with food grade surfactants to change their hydrophobicities and/or hydrophilicities to provide control over the degree of coating on the floss.

While not being limited to a particular theory, the exemplary floss dispensers can: a) deliver actives for tooth and gum therapy/treatment; b) provide sensitivity relief or treatment; c) help re-mineralize and shield teeth from further acid attack through use of re-mineralizing actives; d) deliver anti-bacterial or anti-attachment polymers onto the floss string to delay growth of plaque on surface; and e) be coated with liquids that can boost removal of plaque between teeth by dissolution.

Embodiments of the invention are further described in the following examples. The examples are merely illustrative and do not in any way limit the scope of the invention as described and claimed.

Referring now to the drawings, wherein like reference numbers refer to like parts, there is shown at 10 in FIG. 1 an exemplary embodiment of a dental floss dispenser constructed in accordance with the invention. The dispenser 10 includes a housing 12 and a cover 14, with the housing 12 shown as an integral unit molded and/or snapped together to form a container for both the floss and the oral care fluid. If desired, the cover 14 may be attached to the housing 12 by a hinge 16 and tab 18 snap fitted to the housing 12 to close the cover, and liftable to open the cover 14 and expose the floss 20 (FIG. 2).

The housing 12 and cover 14 are formed of any suitable material, e.g., a plastic or polymeric material, such as, but not limited to, polyvinyl chloride (PVC), polyethylene terephthalate (PET), etc., or any other material known for use in dental floss packaging. The material making up the housing 12 and cover 14 may comprise a combination of materials, including transparent, partially transparent, semi-transparent, opaque and/or non-transparent materials and may be formed in any manner, such thermoforming, injection or molding.

Figure 2:
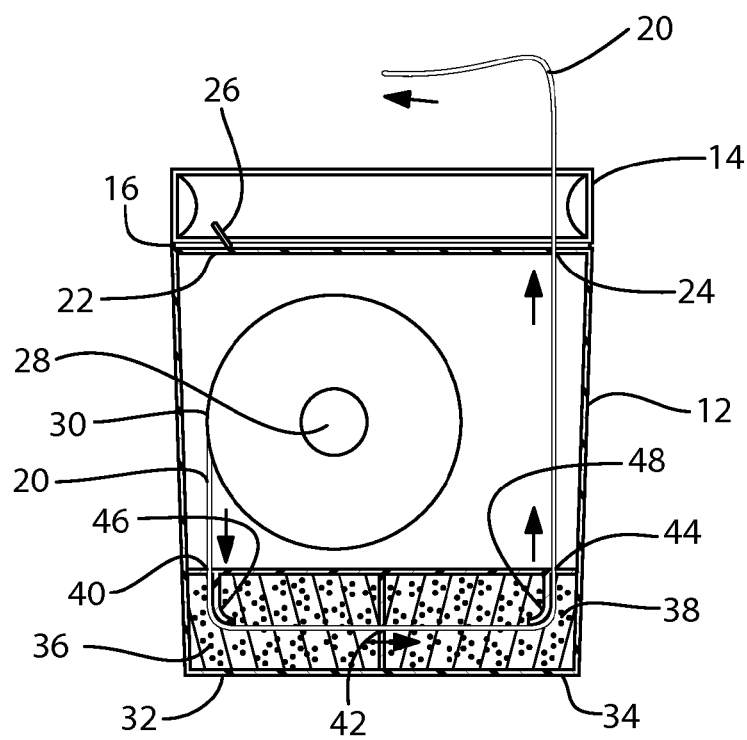
FIG. 2 is an enlarged sectional view along line 2-2 of FIG. 1.

FIG. 2 depicts the dental floss dispenser 10 of FIG. 1 in cross-section with the cover 14 open and the top 22 of the housing 12 having a strand of dental floss 20 emerging from an aperture 24 (floss access port). The top 22 of the housing 12 typically also includes a detent 26 (FIG. 3) for cutting and capturing the cut end of the floss 20. Any suitable length of floss 20 may be pulled out of the aperture 24 and anchored and cut under the cutting detent 26 for use.

Still referring to FIG. 2, the housing 12 includes an internally extending post 28 that is shaped, proportioned, and formed to receive a spool 30 of the floss 20, which preferably is unwaxed. The invention is not so limited however and the floss 20 may be waxed or otherwise coated prior to packaging in the dispenser. The housing 12 also includes first and second fluid storage containers 32, 34 integrally formed for containing first and second porous pads 36, 38 impregnated with or holding at least one oral care fluid. In particular, the first fluid storage container 32 has a first hole 40 and a second hole 42 that are dimensioned to receive the floss 20 preferably without disturbing the lay of the floss fibers. The second fluid storage container 34 shares the second hole 42 with the first fluid storage container 34, and also includes a third hole 44 dimensioned to receive the strand of floss preferably without disturbing the lay of the floss fibers. Both the first and second fluid storage containers 32, 34 further include a respective guide member 46, 48 preferably of plastic or polymeric material. The first guide member 46 extends into the first fluid storage container 32 from adjacent the first hole 40 to help guide the floss 20 between the first hole 40 and the second hole 42. Similarly, the second guide member 48 extends into the second fluid storage container 34 adjacent from the third hole 44 to help guide the floss 20 through the second porous pad 38 of the second fluid storage container between the second hole 42 and the third hole 44.

As noted above, the porous pads 36, 38 are absorbent wicking members that maintain the respective oral care fluid within the fluid storage containers 32, 34 absent attachment to the floss 20. In other words, the porous pads 36, 38 do not overcoat the floss 20, and thereby keep the activated floss 20 drip free. Therefore, the first, second and third holes 40, 42, 44 are dimensioned to receive the floss 20, but are not required to be liquid proof or squeeze the strand of floss 20 in a manner that increases the friction on the floss 20 as it is pulled within the housing 12.

To load the respective oral care fluids onto the floss 20 to activate the floss 20, it is only necessary to pull the floss strand 20 from the spool 30, through the holes 40, 42, 44 and porous pads 36, 38 in the fluid storage containers 32, 34 and out of the aperture 24. As the floss 20 travels within the housing 12, the floss 20 passes through the porous pads 36, 38 in the fluid storage containers 32, 34, with the porous pads 36, 38 impregnated with the suitable oral care fluid. It is understood that the porous pads 36, 38 use wicking action to distribute the respective oral care fluid onto the floss 20 to activate the floss 20 with the fluid. Due to the absorbent nature of the wicking porous pads 36, 38, the floss 20 is not soaked excessively with the oral care fluid and thus there is no need to squeeze the strand of floss 20 to remove excess fluid since the porous pads 36, 38 provide this feature of removing excess fluid.

An advantage of this and all of the embodiments of the invention is that the floss 20 drawn through the housing 12 is freshly activated with the oral care fluid or fluids without providing undue stress on the floss 20. Therefore, when the floss 20 is used in a mouth, a fresh supply of the oral care fluid or fluids is transferred to the user's teeth.

While the example of FIGS. 1 and 2 show multiple porous pads 36, 38, it is understood that the invention is not so limited as to a number of wicking members or porous pads. For example, the housing 12 depicted in FIG. 2 could merely include only one wicking member or porous member in one of the fluid storage containers 32, 34 or the container may have only a single fluid storage container having a single porous pad.

Figure 3:
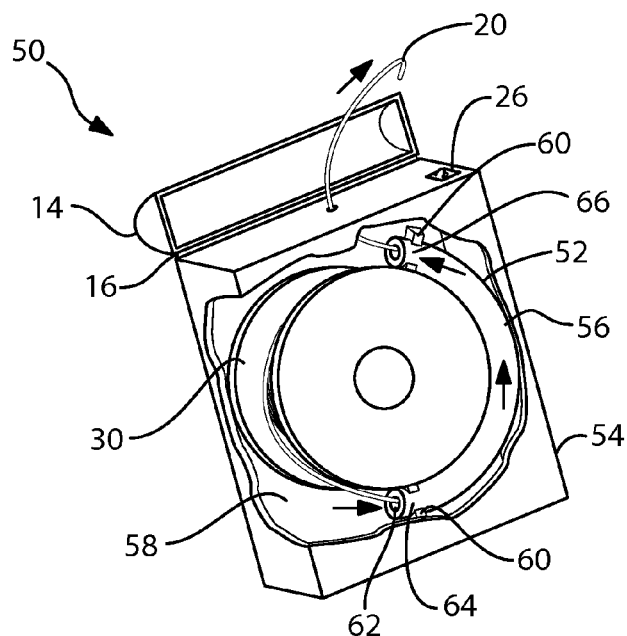
FIG. 3 is a perspective view partially in section of a second exemplary dental floss dispenser constructed in accordance with the invention.

FIG. 3 depicts an exemplary dental floss dispenser 50 similar to the dental floss dispenser 10, and including a single wicking member or porous pad 52 within the housing 54. As can be seen in FIG. 3, the dispenser 50 includes a single fluid storage container 56. The wicking porous pad 52 is secured to an interior wall 58 of the housing 54, preferably by prongs 60 attached to the interior wall 58. The prongs 60 are holding members configured to snugly receive the porous pad 52 preferably placed, but not limited to, a curved alignment about the spool 30. The porous pad 52 includes an interior channel 62 that both serves as a guide member for the floss 20, and as a disturber of the oral care fluid stored by the porous pad 52 onto the floss 20 as the floss 20 is pulled through the channel 62. Preferably, the channel 62 extends throughout the porous pad 52 from the ingress end 64 to the outlet end 66 thereof to provide a regulated flow of the oral care fluid onto the floss.

Figure 4:
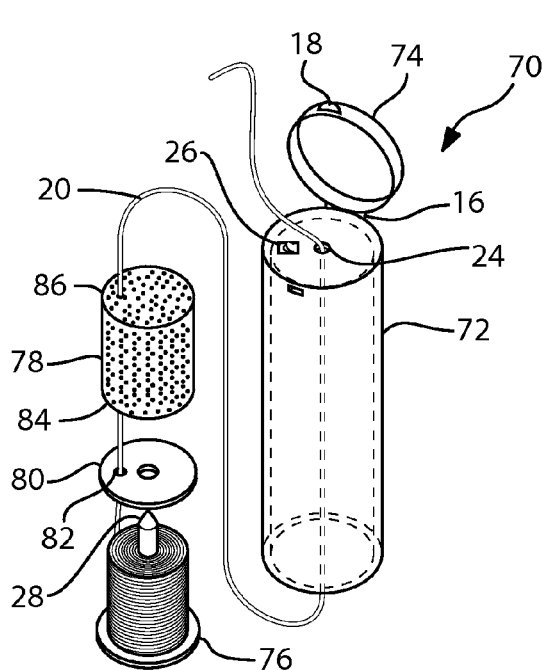
FIG. 4 is an exploded perspective view of a third exemplary dental floss dispenser constructed in accordance with the invention.
Figure 5:
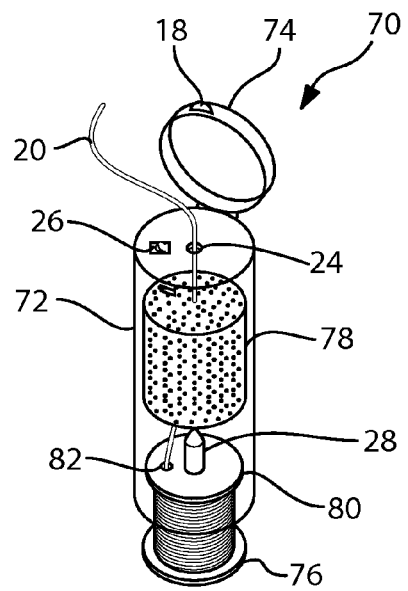
FIG. 5 is a partially exploded perspective view of the dental floss dispenser shown in FIG. 4.

FIGS. 4 and 5 depict another example of the dental floss dispenser in exploded and partially exploded views. In particular, the dental floss dispenser 70 includes a cylindrical tube shaped housing 72 and cover 74. The housing 72 holds a base 76, with the floss 20 coiled on the post 28. The coiled floss is separated from the porous pad 78 by a separator 80 which is preferably a plastic disc or bag. The floss 20 is inserted through a hole 82 of the separator 80 that separates the spool or coil of floss 20 from the fluid storage container which here is the porous pad 78. The floss 20 passes through an ingress end 84 of the pad, through the porous pad 78 and out of its exit end 86. With the porous pad 78 being sufficiently saturated with the oral care fluid as the floss 20 passes through the porous pad 78, the porous pad 78 activates the floss 20 with oral care fluid to thereby impregnate and/or coat the floss. The activated floss is then threaded through the aperture 24 at the top 22 of the housing 72. Again, the aperture 24 does not need to be so tight or restrictive as to provide a fluid tight fit about the floss 20. In fact, the aperture 24 is preferably larger and can be twice or thrice the width of the activated floss due to the absorbent wicking nature of the porous pad 78 so that the porous pad 78 provides protection against unwanted leakage. The cutting detent 26 is placed on the top of the housing 72 and is used for removing a segment of the activated floss.

FIG. 6 depicts an example of the dental floss dispenser having two different floss strings with preferably different oral care fluids and/or benefits that are wound around each other to provide multiple benefits to the user. As can be seen in FIG. 6, the dental floss dispenser 90 includes the cover 14 and housing 92 similar to the previously described housings 12 and 54. In this example, the housing 92 is shown as transparent and includes two posts 28, each receiving a respective spool 30 of dental floss 94, 96 that together form the floss string 20. The housing 92 also includes first and second fluid storage containers, with a first porous pad 98 representing the first fluid storage container and a second porous pad 100 representing the second fluid storage container. A shelf 102 is attached to and extends between opposite planar side walls 104 and 106 of the housing 92 to support the porous pads 98, 100. Preferably, the shelf 102 includes holes there through similar to holes 40 and 44 (FIG. 2) that allow the floss 94 and 96 to pass easily from their spools 30 to their respective porous pads 98 and 100. The floss 94 then passes through the first porous pad 98 and the second floss 96 passes through the second porous pad 100. The separate flosses 94, 96 are individually activated, impregnated or coated as they are dispensed through their respective porous pad and are threaded through a funneling tube 104, which urges the individual activated floss strands 94, 96 into contact with each other to form the dental floss 20. In this manner, the individually activated floss strands 94, 96 are adhered to each other to form the unitary dual treated floss 20. The floss 20 can be cut into segments of desired length using the cutting detent 26, with the second segments impregnated with the adhered compositions of oral care fluid for multiple purposes including whitening the teeth, cleaning the teeth, protecting the teeth and for treatment of gingivitis, etc. The cover 14, which is joined to the housing 92 by the hinge 16 encloses the floss 20 between uses.

While the invention has been described in detail and with reference to specific examples thereof, it would be apparent to one skilled in the art that various changes and modification can be made therein without departing from the spirit and scope thereof. For example, any of the examples can use one or a plurality of porous pads, with each porous pad including an oral care fluid as desired. Without further elaboration, the foregoing will so fully illustrate the invention that others may, by applying current or future knowledge, readily adapt the same for use under various conditions of service.

What is claimed is:

1. A dental floss dispenser comprising:
a housing having an interior cavity and a floss access port;
a spool of dental floss positioned within the interior cavity of the housing; and
an arcuate wicking member containing an oral care fluid, the arcuate member being secured to a wall of interior cavity of the housing so that a concave portion of an outer surface of the arcuate wicking member is directly adjacent to and the wraps around a portion of the spool of dental floss such that opposing first and second ends of the wicking member are arranged adjacent radically opposite portions of the spool wherein a line connecting the first and second ends extends through a center portion of the spool, the arcuate wicking member having a channel extending therethrough between the opposing ends defining an inlet at the first end and an outlet at the second end, the outlet being positioned proximate the floss access port, wherein the dental floss passes through the channel of the arcuate wicking member, passes through the channel and exits from the outlet prior to extending through the floss port.

2. The dental floss dispenser of claim 1, wherein the arcuate wicking member is a porous pad.

3. The dental floss dispenser of claim 2, wherein the porous pad is a sponge.

4. The dental floss dispenser of claim 1, wherein the arcuate wicking member is secured to the wall of the interior cavity of the housing by prongs attached to the wall.

* * * * *